(12) United States Patent
Lopatin

(10) Patent No.: US 7,238,761 B2
(45) Date of Patent: Jul. 3, 2007

(54) MULTIFUNCTIONAL BIOCOMPATIBLE HYDROPHILIC GEL AND THE METHOD OF GEL MANUFACTURE

(75) Inventor: Vladislav Victorovich Lopatin, Moscow (RU)

(73) Assignee: Obschestvos Organichennoy Otvetstvennostyu "Vitagel", Moscow (RU)

( * ) Notice: Subject to any disclaimer, the term of this patent is extended or adjusted under 35 U.S.C. 154(b) by 401 days.

(21) Appl. No.: 10/937,472

(22) Filed: Sep. 9, 2004

(65) Prior Publication Data

US 2005/0054768 A1    Mar. 10, 2005

Related U.S. Application Data

(63) Continuation of application No. PCT/RU02/00164, filed on Apr. 10, 2002.

(51) Int. Cl.
| | |
|---|---|
| *C08F 20/56* | (2006.01) |
| *C08F 22/38* | (2006.01) |
| *C08F 120/56* | (2006.01) |
| *C08F 220/56* | (2006.01) |
| *C08F 222/38* | (2006.01) |

(52) U.S. Cl. .............. 526/303.1; 526/329.7; 424/78.35; 424/78.31; 424/422; 424/423; 424/487

(58) Field of Classification Search ............ 526/303.1, 526/329.7; 424/78.35, 78.31, 422, 423, 487
See application file for complete search history.

(56) References Cited

U.S. PATENT DOCUMENTS

| | | | |
|---|---|---|---|
| 4,769,427 A * | 9/1988 | Nowakowsky et al. ....... | 526/64 |
| 4,939,150 A | 7/1990 | Gashinsky et al. | |
| 5,798,096 A * | 8/1998 | Pavlyk ................. | 424/78.35 |
| 5,863,551 A | 1/1999 | Woerly | |

FOREIGN PATENT DOCUMENTS

| | | | |
|---|---|---|---|
| EP | 1 151 756 A1 | * | 11/2001 |
| GB | 2114578 | | 8/1983 |
| JP | 06-289331 | * | 10/1994 |
| JP | 06-289335 | * | 10/1994 |
| RU | 2122438 | | 11/1998 |
| RU | 2 127 129 C1 | | 3/1999 |
| RU | 2165263 C1 | | 6/2000 |
| RU | 2152800 C1 | | 7/2000 |
| WO | 01/49336 A1 | | 7/2001 |
| WO | 02/16453 A1 | | 2/2002 |

OTHER PUBLICATIONS

Esp@cenet English Abstract of RU 2067873 of Oct. 1999.
English Abstract and claims of RU 2122438 of Nov. 1998.
Esp@cenet English Abstract of RU152800 of Jul. 2000.
Esp@cenet English Abstract of RU21655263 of Apr. 2001.
Esp@cenet English Abstract of RU 2127129 of Mar. 1999 and claims.
Esp@cenet English Abstract of WO8101290 of May 1981.
Esp@cenet English Abstract of WO8805794 of Aug. 1988.
English Abstract of WO8809349 or Dec. 1988.
English Abstract of EP0315690 of May 1989.
Title page and claims of WO99/10021 of Mar. 1999.
Shekhter, A. B, et al., "Injectable hydrophilic polyacrylamide gel Formacryl and tissue response to its implantation", *Annuls of Plastic, Reconstructive and Esthetic Surgery*, No. 2 pp. 11-21, 1997.
Savitskaya, M. N., et al., "Polyacrylamide", *Tecnika*, p. 113, 1969.

* cited by examiner

*Primary Examiner*—Ling-Sui Choi
(74) *Attorney, Agent, or Firm*—Ladas and Parry LLP

(57) ABSTRACT

Multifunctional biocompatible hydrophilic gel contains, in % (w/w), acrylamide—1.95-8.0, methacrylamide—0.54-3.0, 2-hydroxyethyl methacrylate—0.003-0.4, N,N'-methylene-bis-acrylamide—0.006-0.6 and water—q.s. to 100. The hydrophilic gel is produced by co-polymerization of the above mentioned monomers in water medium in the presence of a peroxide initiator of polymerization in three stages which include (1) incubation of the reaction mixture at 20-30° C. for 12-24 hours, (2) exposure to γ-radiation at a dose of $0.4\text{-}1.0 \times 10^6$ rads, and (3) incubation at a temperature of 100-130° C. and pressure of 0-1.2 atm. for 20-40 minutes.

8 Claims, 2 Drawing Sheets

30 мкм

MULTIFUNCTIONAL BIOCOMPATIBLE HYDROPHILIC GEL AND THE METHOD OF GEL MANUFACTURE

This is a continuation of copending International Application PCT/RU02/00164 filed on Apr. 10, 2002, which designated the U.S., claims the benefit thereof and incorporates the same by reference.

FIELD OF ENGINEERING

The invention concerns the formulation and the method of manufacture of a biocompatible polyacrylamide gel that can be used as material for medical purposes, in particular as a carrier for human and animal cells implanted into a mammal's body;

as depot for drugs in long-term pharmacotherapy, as in case of tumors or abscesses.

Prototypes

Polyacrylamide hydrophilic gels (PAAG) are known to be rather inexpensive and easy in manufacturing and chemically and biologically inactive. It is easy to synthesize gels of desirable density and in a form suitable for injections, subcutaneous and/or in soft tissues, with minimal injury to patient's body.

In medicine, a method is known of treatment of insulindependent diabetes (RU 2165263) by transplantation of the heterogeneous β-cells of the pancreas into a polyacrylamide gel previously inserted into the patient's tissue, through subcutaneous injection for instance, around which a capsule is formed.

Another method is known of culturing mammal's heterogeneous cells (RU 2152800), especially Leydig's and melanoma cells, in a polyacrylamide gel previously implanted into a mammal's body.

This makes it possible to treat a number of diseases by the way of transplantation into the patient's body of heterogeneous cells capable of producing enzymes and/or hormones essential for the recipient, as well as to administer vaccine therapy against oncology diseases.

However, it was found experimentally that the time during which the implanted heterogeneous cells remain physiologically active depends on the properties of the polyacrylamide gel (PAAG), other things being the same.

A connective tissue capsule is known to form around the PAAG implanted into a mammal's body (A. B. Shekhter et all "Injectable hydrophilic polyacrylamide gel Formacryl and tissue response to its implantation", in "Annals of plastic, reconstructive and esthetic surgery", 1997, No. 2, p. 19), which prevents T-lymphocytes from contacting the implanted heterogeneous cells for some time and thus protects these cells against being killed.

However, the formation of a connective tissue capsule is not the only factor influencing the time of physiological activity of the implanted heterogeneous cells in a recipient's body.

A biocompatible polyacrylamide gel is known and described in application EP [1] 742022, which contains from 3.5 to 9.0% (w/w) of a cross-linked copolymer of acrylamide with methylene-bis-acrylamide as cross-linking agent and 96.5-99.0% (w/w) of water.

The gel is produced by the method described in the same application (EP [1] 742022) that involves co-polymerization of acrylamide with methylene-bis-acrylamide in an aqueous medium in the presence of peroxide initiators of polymerization. To obtain a cross-linked copolymer, the reaction mixture is incubated at room temperature for 20 minutes. The process is run in one stage, with the use of a mixture of ammonium persulfate and tetramethylethylene diamine as a peroxide initiator of polymerization and apyrogenic water or sodium chloride solution as aqueous medium.

The hydrophilic gel obtained by this method has a low degree of cross-linking of the polymer, which is a result of one-stage low-temperature co-polymerization. This allows the connective tissue to grow quickly into the inserted gel and leads to fast shrinking and resorption of the latter (A. B. Shekhter et all "Injectable hydrophilic polyacrylamide gel Formacryl and tissue response to its implantation", in "Annals of plastic, reconstructive and esthetic surgery", 1997, No. 2, p. 19).

In addition, the hydrophilic gel obtained by this method contains unbound molecules of tetramethylethylene diamine, free $NH_2$-radicals and acrylamide monomers in amounts of 1.0-1.2 μg per g of polymer (1.0-1.2 ppm) which may cause an active aseptic inflammatory reaction at an early stage of gel implantation (A. B. Shekhter et all "Injectable hydrophilic polyacrylamide gel Formacryl and tissue response to its implantation", in "Annals of plastic, reconstructive and esthetic surgery", 1997, No. 2, p. 19).

A biocompatible hydrophilic gel is known and described in patent RU [1] 2127129, which contains from 1.0 to 8.0% (w/w) of a cross-linked copolymer of acrylamide with methylene-bis-acrylamide as cross-linking agent and 92.0-99.0% (w/w) of water. A method for manufacturing this gel also is described in patent RU [1] 2127129 and involves co-polymerization of acrylamide with methylene-bis-acrylamide in an aqueous dispersion medium in the presence of a peroxide initiator of polymerization. The aqueous medium is obtained by electrolysis of water and has pH 9.0-9.5. The cross-linking of copolymer is run in two stages by incubating the reaction mixture first at 20-90° C. for 2-24 hours and then at 100-105°Ñ for 2-4 hours.

The hydrophilic gel obtained by the above mentioned method is free from tetramethylethylene diamine and contains just higher than 1% of $NH_2$-radicals and 0.6-0.8 μg of acrylamide monomers per g of polymer (0.6-0.8 ppm). However, it is also designed and intended chiefly for plastic contour correction of bodily defects and, as a carrier, is not able to maintain the physiological activity of the implanted heterogeneous cells long enough.

DISCLOSURE OF THE INVENTION

The applied invention is primarily aimed at increasing the time of physiological activity of heterogeneous cells placed in a polyacrylamide gel when in a recipient's body.

The second goal is to reduce resorption of a hydrophilic gel and make it less permeable for macrophages after implantation into a recipient's body.

The third goal is to reduce tissue response to gel implantation by minimizing the contents of free radicals and monomers in a hydrophilic gel.

The problems are solved by proposing a multifunctional biocompatible hydrophilic gel consisting of polyacrylamide and water, which, according to the invention, it contains as the polyacrylamide a cross-linked copolymer of acrylamide, methacrylamide and cross-linking agents—2-hydroxyethyl methacrylate and N,N'-methylene-bis-acrylamide.

The above-mentioned polyacrylamide contains components in the following proportions, in % (w/w):

acrylamide—65.0-80.0, methacrylamide—18.0-30.0, 2-hydroxyethyl methacrylate—0.1-4.0

N,N'-methylene-bis-acrylamide—0.2-6.0.

The above mentioned polyacrylamide makes up from 3.0 to 10.0% (w/w) of the total weight of the biocompatible hydrophilic gel.

The above-mentioned biocompatible gel contains components in the following proportions, in % (w/w):

acrylamide—1.95-8.0, methacrylamide—0.54-3.0, 2-hydroxyethyl methacrylate—0.003-0.4, N,N'-methylene-bis-acrylamide—0.006-0.6, water—sufficient quantity (hereafter q.s.) to 100.

The hydrophilic gel contains bidistilled apyrogenic water as the water.

The multifunctional biocompatible hydrophilic gel has pH 3.5-4.5.

The above-mentioned hydrophilic gel is suitable for injection and packed in syringes.

The above mentioned hydrophilic gel is easy for capsules to form around it in a human or animal body, for which purpose it is implanted into the human or animal body, with subsequent placement of a selected cell culture into it.

The above mentioned goals are also accomplished by proposing a method for manufacturing a multifunctional biocompatible hydrophilic gel by the way of multistage copolymerization of monomers with cross-linking agents in an aqueous medium in the presence of a peroxide initiator of polymerization, in which, according to the invention, acrylamide and methacrylamide as monomers and 2-hydroxyethyl methacrylate and N,N'-methylene-bis-acrylamide as cross-linking agents are taken in the following proportions, in % (w/w):

acrylamide—1.95-8.0, methacrylamide—0.54-3.0, 2-hydroxyethyl methacrylate—0.003-0.4, N,N'-methylene-bis-acrylamide—0.006-0.6, water—q.s. to 100, and copolymerization is run in three stages which include (1) incubation of the reaction mixture at 20-30° C. for 12-24 hours, (2) exposure to γ-radiation at a dose of $0.4-1.0 \times 10^6$ rads, and (3) incubation at a temperature of 100-130° C. and pressure of 0-1.2 atm. for 20-40 minutes.

After the first stage of copolymerization, the half-finished product is washed with hot water with a temperature of 70-110° C. for at least 3 hours at a pressure of 0-1.2 atm., the gel and water being taken in the ratio by weight 1:8-10.

Hydrogen peroxide and/or ammonium persulfate used as initiators of copolymerization are added at the rate of no more than 0.33% (w/w) of the total weight of starting materials.

Bidistilled apyrogenic water is used as aqueous medium.

The gel obtained by this method is placed or packed in syringes and used for implantation into a human or animal body where it becomes a basis for formation of a capsule and serves as a carrier for subsequently placed selected cell cultures.

The applied hydrophilic gel can be produced by different methods, and the applied method in no way excludes other approaches to its making, either direct or indirect, and presents one of possible ways of manufacturing a hydrophilic gel of the given composition and properties.

Obviously biological active properties of a hydrogel made on the basis of a three-dimensional net of monomers cross-linked by cross-linking agents will largely depend on the structure of the cross-linked polymer.

The structure of the cross-linked polyacrylamide, in turn, will depend on the conditions its synthesis, namely, (1) the quality and proportions of the starting materials, including cross-linking agents and initiators of polymerization which fit into the copolymer structure (at NH—, CH—, COOH—, $NH_2$— and $CH_2$-groups) by means of chemical and hydrogen bonds, and (2) the mode of polymerization. This is because the cross-linking process is known to produce substantial changes in physical and chemical properties of polyacrylamide derivatives, caused by branching of the main chains, formation of cross-linked structures, and partial destruction (see Savitskaya, M. N., and Kholodova, Yu. D. *Polyacrylamide*, Tekhnika Publishing House, 1969, p. 113).

The substance of the invention lies in that the formulation of a polyacrylamide gel and the operating conditions of co-polymerization are chosen, which serve to increase the time of physiological activity of heterogeneous cells when in a recipient's body.

The use of the applied method for manufacturing the applied polyacrylamide gel allowed a final product to be obtained with fewer unbound amino groups, free $NH_2$-radicals and unsaturated double bonds. Also, a higher degree of cross-linking is achieved as a result of both formation of structural groups such as (—$H_2$C—NH—$CH_2$—), (—CO—NH—$CR_2$—O—R), (—CO—NH—NH—CO—), (H—COR—NH—CR—O—R), (—CONH—R—NH—CO), where R is $CH_3$, $CH_2$, $NH_2$, $C_2H_5$, or $C_3H_7$, and an increase in number of cross links, i.e. N—N bonds.

All this taken together made it possible to obtain a hydrophilic gel with higher resistance to resorption and shrinking while in a recipient's body, and to create conditions for survival of the cells placed in the gel.

BRIEF DESCRIPTION OF FIGURES

To help better understanding of the invention, below are given particular examples of how the applied biocompatible hydrophilic gel is produced, where.

Figure 2A:
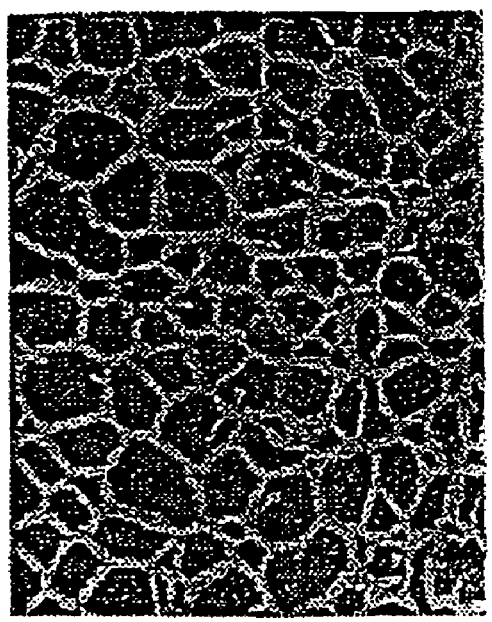
Figure 2B:
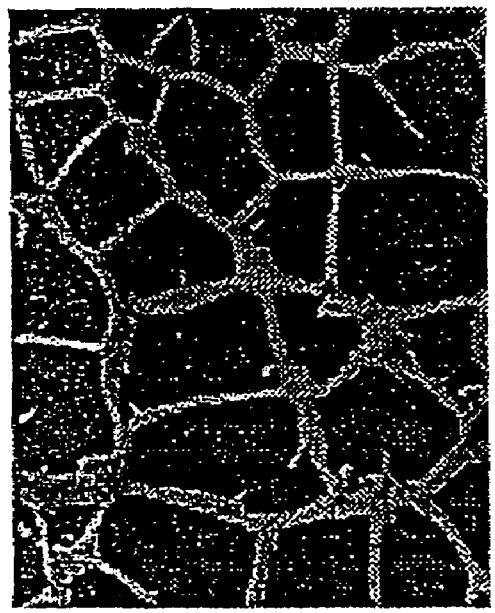

Both IR spectra are obtained at 4000-500 $cm^{-1}$. (Wave lengths ($cm^{-1}$) are plotted as abscissas, and absorption rates T (%) are plotted as ordinates);

FIG. 2a presents a picture of the applied hydrophilic gel obtained by scanning electron microscopy (SEM);

FIG. 2b presents a picture of the Formacryl gel obtained by scanning electron microscopy (SEM);

Both pictures are made using an electron microscope Hitachi S 405A.

EXAMPLES OF EXERCISE OF THE INVENTION

Reagents used for manufacture of the applied biocompatible hydrophilic gel:

Acrylamide: $C_3H_5NO$, molecular weight 71.08, white crystalline odorless powder; melting point 84.5°Ñ; supplied by Sigma (Catalogue <<Biochemicals and reagents for molecular biology and life sciences research>> SIGMA, 1999, p. 47, cat. No.À8887);

Methacrylamide: $C_3H_7NO$; molecular weight 73.08, white powder; melting point 111° C.; supplied by Fluka (Fluka Katalogue "Chemica-Biochemica", Fluka AG, Switzerland, 1986/87, p. 1151);

2-hydroxyethyl methacrylate: $C_6H_{10}O_3$, molecular weight 130.1, liquid; boiling point 205-208° C.; density 1.07 g/ml; supplied by Sigma (Catalogue <<Biochemicals and reagents for molecular biology and life sciences research>> SIGMA, 1999, p. 567, cat. No. H8633);

N,N'-methylene-bis-acrylamide: $C_7H_{10}N_2O_2$, molecular weight 154.16, white crystalline odorless powder; melting point 185° C., supplied by Sigma (Catalogue <<Biochemicals and reagents for molecular biology and life sciences research>> SIGMA, 1999, p. 696, cat. No. M7256);

Ammonium persulfate: $(NH_4)_2 S_2O_8$—molecular weight 228.19; colorless plane crystals; breaking temperature 120° C.; supplied by Sigma (Catalogue <<Biochemicals and reagents for molecular biology and life sciences research>> SIGMA, 1999, p. 117);

Hydrogen peroxide: $H_2O_2$— molecular weight 34.0; colorless liquid, density at 0°Ñ −1.465; melting point −0.89° C.; supplied by Sigma (Catalogue <<Biochemicals and reagents for molecular biology and life sciences research>> SIGMA, 1999, p. 556, cat. No. H6520).

All the above mentioned monomers must be of biological grade and suitable for use without additional purification.

Water must be bidistilled and apyrogenic (pH=5.6).

The method is exercised as follows:

To prepare a reaction mixture, bidistilled apyrogenic water with pH 5.6 is taken.

An aqueous solution is prepared which contains acrylamide, methacrylamide, 2-hydroxyethyl methacrylate and N,N'-methylene-bis-acrylamide taken in the ratio 65.0-80.0: 18.0-30.0:0.1-4.0:0.2-6.0.

The starting monomers make up from 3.0 to 10.0% of the total weight of solution. (By varying proportions between monomers in the starting mixture, hydrophilic gels of different densities and elasticities can be obtained).

To the obtained solution is added an initiator of polymerization which is either hydrogen peroxide 0.1-0.3% (w/w) or ammonium persulfate 0.0006-0.03% (w/w) or a mixture of both of them taken in any proportions but in the amounts not to exceed the sum of their maximal values. By varying proportions between hydrogen peroxide and ammonium persulfate, hydrophilic gels with pH-values in the range from 3.5 to 4.5 are obtained.

The prepared reaction mixture is caused to pass through antiseptic polymer filters, such as F8273, with filtration rating of 0.45 mm CA/CN (Sigma, USA), and then incubated at 20-30° C. for 12-24 hours for co-polymerization of the starting monomers. After that, the obtained half-finished product, which looks like a gel by that time, is washed with hot water. For this purpose, it is placed in a vessel with water with a temperature of 70-110° C. at a pressure of 0-1.2 atm. for 4-6 hours, the gel and water being taken in the ratio 1:8-10.

This is followed by the second stage of co-polymerization for which purpose the half-finished product is exposed to y-radiation at a dose of $0.4-1.0 \times 10^6$ rads. After that, the half-finished product is packed into bottles or syringes, and the third stage of co-polymerization is carried out by incubating the gel at 120° C. and 1.2 atm. for 20-40 minutes.

Studies of physicochemical and chemical characteristics and toxicity of the applied hydrophilic gel were conducted in accordance with ISO Standards 10993 "Biological Evaluation of Medical Devices", "Guidelines on Sanitary and Hygienic Assessment of Medical Rubber and Latex Devices" (USSR Ministry of Health, M., 1988) and Guidelines "Allowable Migration of Chemical Substances Contacting Food Hydrophilic Gels and Assay Methods", SanPiN 42-122-42-40-86 (Sanitary and Hygienic Regulations).

Assays of acrylamide monomers and N,N'-methylene-bis-acrylamide in the obtained hydrophilic gel were made following a procedure described in V. V. Kuznetsov et al. <<Determination of Acrylamide in Polyacrylamidic gels">// The 52-nd Pittsburgh Conference on Analytical Chemistry and Applied Spectroscopy.—New Orleany, La., 2001, Abstract Book, [1] 1648.

In these studies, the applied hydrophilic gel was found to have the following characteristics:

Appearance—gel;
Color—from colorless to semitransparent opal;
Refraction index—1.328-1.360;
Density—1.0-1.2 $g/cm^3$;
pH—3.5-4.5;
Monomer contents—up to 0.4 ppm;
Bromine value—max. 1.0 (mg of bromine per 1).
Chemical studies showed that:
no migration of metals (Cu, Fe, Ni, Zn, Al, Ti, Ag) from the hydrophilic gel to an aqueous extraction determined by the atomic absorption method is found within response limits of the analytical method (0.02; 0.05; 0.05; 0.02; 0.005; 0.04 mg/l, respectively), which values are much lower that the corresponding maximal permissible concentrations set for potable water;
migration of sodium does not exceed 0.12 mg/l, which is lower than the maximal permissible concentration of 200 mg/l set for potable water.

In vitro studies of toxicity on rabbit isolated red blood cells did not reveal any hemolytic effect of aqueous extractions from the hydrophilic gel. The hemolytic index was found to be 0.04% vs. 2% set as permissible limit.

In a study of acute toxicity on white mice, no case of death or appearance of clinical signs of intoxication in the animals was reported after parenteral administration of the hydrophilic gel at a dose of 50.0 ml/kg body weight: there were no differences in general condition, behavior, food uptake and hair condition as compared to controls.

In a study after dissection of the mice, the status of tissues at the site of injection, regional lymphatic nodes, the internal organs condition (liver, kidneys, spleen) were found normal.

No statistically significant differences in body weight gain, clinical and biochemical blood test results, internal organs' condition were found between the animals with subcutaneously injected gel and controls 2.5 months post-injection.

No sensitizing effect of the hydrophilic gel was found in mast cell degranulation immunological test (MCDIT).

Micronuclear tests of the bone marrow preparations did not reveal any mutagenic effect of the hydrophilic gel. A histological assessment of the tissue samples taken at the site of injection and from the internals (liver, kidneys, spleen, testes) showed a mild tissue response only during the first days after the transplantation and no dystrophic or necrotic changes in the internals.

Examples of manufacture and use of the applied biocompatible hydrophilic gel as a carrier for culturing heterogeneous cells in a recipient's body are given below.

Example 1

To produce a hydrophilic gel, 11.2 g of acrylamide, 3.6 g of methacrylamide, 0.48 g of 2-hydroxyethyl methacrylate and 0.72 g of N,N'-methylen-bis-acrylamide, all of biological grade, were dissolved in 384 ml of bidistilled apyrogenic water with pH 5.6. After that, 0.04 g of ammonium persulfate and 2 ml of 30% hydrogen peroxide were added. The reaction mixture was caused to pass trough an antiseptic polymer filter F8273 with filtration rating of 0.45 mm CA/CN (Sigma, USA) and placed in a water bath for incubation at 30° C. for 22 hours.

After that, the half-finished product, which looked like a gel by that time, was washed with hot water at 90° for 4 hours, water and gel being taken in the ratio 10:1. This was followed by the second stage of co-polymerization for which purpose the half-finished product was exposed to γ-radiation at a dose of $0.8$-$1.0 \times 10^6$ rads. After that, the half-finished product was packed into 0.5-3.0 ml syringes, and the third stage of co-polymerization was carried out by incubating the product at 120° C. and 1.2 atm. for 30 minutes.

The obtained gel contains 96% (w/w) of water and 4% (w/w) of copolymer in which for 70.0% (w/w) of acrylamide there are 22.5% (w/w) of methacrylamide, 0.3% (w/w) of 2-hydroxyethyl methacrylate and 0.4% (w/w) of N,N'-methylene-bis-acrylamide, and has pH=4.3.

The obtained hydrophilic gel has the following physico-chemical characteristics:

Appearance—colorless, semitransparent, opal gel;
Refraction index—1,348;
pH—4.3;
Density—1.0 g/cm$^3$;
Monomer contents 0.1 ppm;
Bromine value—0.1 (mg of bromine per 1).

Dried samples of the hydrophilic gel were studied by IR spectroscopy and electron microscopy. A corresponding IR spectrum and picture are presented in FIGS. 1a and 2a.

To compare, FIGS. 2b and 2b present an IR spectrum and chromatogram obtained for an extract of a prototype gel Formacryl produced in Russia under patent RU [1] 2127129. It contains 96% (w/w) of water and 4% (w/w) of copolymer in which for 96% (w/w) of acrylamide there are 4.0% (w/w) of N,N'-methylene-bis-acrylamide, has pH=5.4 and bromine value 0.27 (mg of bromine per 1) and is obtained by incubation of the starting monomers with hydrogen peroxide and ammonium persulfate added at the rate of 0.3% (w/w) in two stages, first at 60° C. for 12 hours and after that at 100° C. for 2 hours.

Figure 1A:
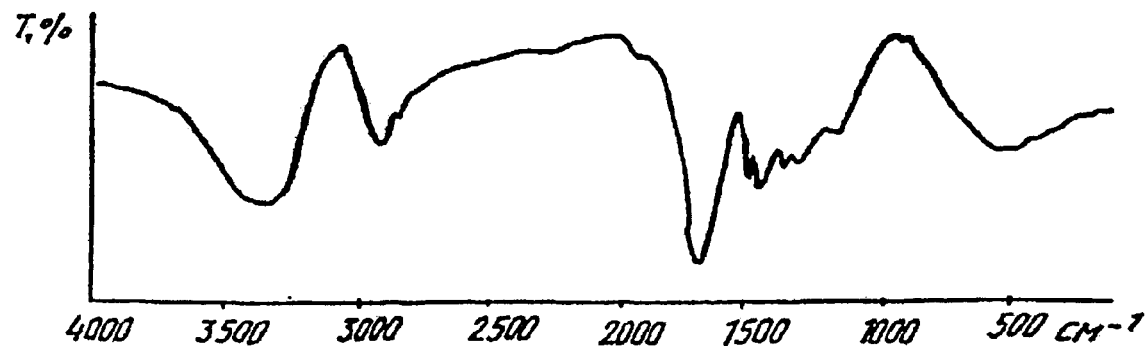
FIG. 1a presents an infrared (IR) absorption spectrum obtained for the applied hydrophilic gel.

As it can be seen from FIG. 1a, there is no peak at 1620 cm$^{-1}$ on the spectrum presented, evidencing the absence of free NH$_2$-radicals which are capable of fitting into the structure by means of coordinate bonding.

Figure 1B:
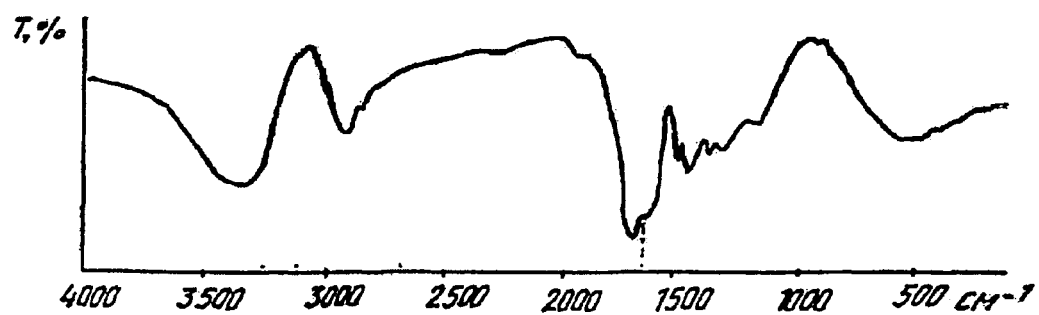
FIG. 1b presents an IR absorption spectrum obtained for a prototype gel "Formacryl" produced in Russia under patent RU [1] 2127129.

By contrast, the spectrum on FIG. 1b does have a peak at 1620 cm$^{-1}$, indicating to the presence of free NH$_2$-radicals in amounts somewhat more than 1%.

For electron microscopic studies, samples of the applied hydrophilic gel and the Formacryl gel made as described above were dried until constant weight and looked as film. The structure of hydrophilic gels was studied by scanning electron microscopy (SEM) using an electron microscope Hitachi S 405A. The preparations for microscopic examination were made by cutting off from samples of the tested hydrophilic gels dried and then frozen in liquid nitrogen. Before scanning, the surface of the preparations was sprayed with gold.

Pictures of the applied hydrophilic gel and the Formacryl gel obtained by the method of scanning electron microscopy (SEM) are presented in FIGS. 2a and 2b, respectively.

As it can be seen from FIG. 2, the applied hydrophilic gel has more close-meshed structure than Formacryl.

Example 2

Use of the applied hydrophilic gel as a carrier for culturing xenogenic tumor cells.

One ml of the hydrophilic gel produced as described in Example 1 was injected underneath the skin to Ñ57 Black line mice. After a connective tissue capsules had formed around the gel 1.5 months post-injection, 1 mln. human melanoma SKMEL-1 line cells were implanted into each gel capsule.

Gel capsules were extracted in 3, 6 and 9 months, and the human melanoma cells were tested for viability and physiological activity.

The human melanoma SKMEL-1 line cells were found to be viable even after 9 months of being cultured in the capsules of the applied gel.

After isolation of the melanoma cells from the capsule and transfer into the culture, it was found, using a standard procedure of polymerase chain reaction, that conservative human myoglobin in the melanoma cells grown in a standard broth was identical to that in the cells which had been cultured for 9 months in a capsule of the hydrophilic gel in a mouse's body.

This example shows that the applied hydrophilic gel can be used as a carrier for long-term culturing of the cell implanted into a recipient's body and maintain them viable for a long time.

Example 3

Use of the applied hydrophilic gel as a carrier for the porcine Leydig's cells implanted into a human body for the treatment of infertility.

The hydrophilic gel produced as described in Example 1 was inserted into the tissues of male patients. Following formation of a connective tissue capsule, the Leydig's cells taken from pigs at the age of puberty were implanted.

Blood testosterone levels were measured with a diagnostic kit supplied by KhemaMedika (Russia) following manufacturer's instructions.

Testosterone levels measured after the implantation of the porcine Leydig's cells are given in the Table below.

TABLE

| Testosterone levels | 0 months | 3 months | 6 months | 10 months | 12 months | 16 months | 22 months |
|---|---|---|---|---|---|---|---|
| Duration of culturing of Leydig's cells in the applied hydrophilic gel | | | | | | | |
| 1$^{st}$ patient 52 years | 4.8 nmol/l | 8.6 nmol/l | 10.8 nmol/l | 16.0 nmol/l | 12.0 mol/l | 16.2 mol/l | 18.0 mol/l |
| 2$^{nd}$ patient 38 years | 6.8 mol/l | 12.6 mol/l | 16.4 mol/l | 18.6 mol/l | | 22.4 mol/l | |

TABLE-continued

| Testosterone levels | 0 months | 3 months | 6 months | 10 months | 12 months | 16 months | 22 months |
|---|---|---|---|---|---|---|---|
| Duration of culturing of Leydig's cells in the Formacryl hydrophilic gel (prototype gel) | | | | | | | |
| 3rd patient 50 years | 3.8 mol/l | 5.8 mol/l | 10.8 mol/l | 10.6 mol/l | 8.0 mol/l | 6.2 mol/l | 0 |
| 4th patient 6 years | 5.6 mol/l | 8.6 mol/l | 13.4 mol/l | 12.6 mol/l | 9.5 mol/l | 8.4 mol/l | 5.2 mol/l |

As it can be seen from the Table, the applied hydrophilic gel can be successfully used as a carrier for the porcine Leydig's cells implanted into a human body which remained capable of producing testosterone for 22 months, while the cells implanted into a prototype gel (Formacryl) showed a decline in the synthesis of testosterone as early as after 10 months.

Example 4

Use of the applied hydrophilic gel as a carrier for heterogeneous cells of the pancreas implanted into a human body for the treatment of insulindependent diabetes.

1. Female patient F., 37 years. A diagnosis of insulindependent diabetes was made 17 years ago, 1 year post-childbirth.

The pregnancy was abnormal and accompanied by toxemia in the second half of gestation, nephropathy and a substantial gain in weight (up to 26 kg). Since the onset, the course of disease was unstable which made it difficult to choose an adequate insulin therapy. Exogenous insulin uptake varied from 58 to 30 units/day. For two last years, pathological changes in the kidneys have been diagnosed and are identified as diabetic nephropathy. The urinary protein levels exceeded the upper limit of proteinuria 10- and even 12-fold. Blood pressure increased to 170/110 Hg mm.

The hydrophilic gel produced as described in Example 1 was inserted into the patient's tissue. Following formation of a connective tissue capsule, newborn rabbit pancreatic cells were implanted into the gel.

Seven days post-implantation of the pancreatic cells, the patient reported an improvement in general condition. She felt less thirsty and experienced less pronounced sensation of dryness in the mouth. Blood pressure fell to 140/90 Hg mm. On day 15 post-implantation, the dose of exogenous insulin was reduced from 30 units to 18 units (blood and urine control) because of further improvement in the patient's condition. The need in exogenous insulin fell to 12 units/day thirty days after implantation and to 4 units/day by the end of the second month.

The patient has been followed up for 12 months after implantation of the pancreatic cells. No clinical signs of diabetic nephropathy are found, blood pressure is within normal range for age. The patient is transferred to peroral hypoglycemic drugs and recommended to strictly follow antidiabetic diet and have blood and urine glucose and glycosylated hemoglobin levels regularly measured.

2. Male patient K, 52 years. Insulindependent diabetes was diagnosed at the age of 18 years and was heavy stress-related. At an early stage, the patient's condition was unstable severe. The doses of exogenous insulin were as high as 70 units/day. Afterwards, however, the course of disease became more stable, with symptoms aggravating in stress situations or as a result of non-compliance with dietary recommendations.

A deterioration of the vascular status of lower extremities, reduction in libido, erectile dysfunction, deterioration of quality of sexual intercourse have been observed for the last three years. Diabetic angiopathy of lower extremities and penis was diagnosed. During the last year, the requirements in exogenous insulin varied from 20 to 40 units/day.

The hydrophilic gel produced as described in Example 1 was inserted into the patient's tissue. Following formation of a connective tissue capsule, 14-day pig pancreatic cells were implanted into the gel.

An improvement in general condition was reported two weeks after implantation of the pancreatic cells. The need in exogenous insulin decreased to 12 units/day one month and to 6 units/day two months post-implantation. After 4 months, the patient was transferred to peroral hypoglycemic drugs. Sexual life normalized, and the vascular status of lower extremities improved.

Assessment of both subjective and objective symptoms and results of laboratory tests of the patients under consideration suggest a high efficacy of the treatment of diabetes by insertion of heterogeneous cells of the pancreas into the hydrophilic gel of the applied composition.

The therapeutic effect usually persists during 10-20 months, depending on disease severity. The number of cells to be implanted also depends on the severity of diabetes, in particular on the dose of exogenous insulin taken.

INDUSTRIAL APPLICATION

To conclude, the above mentioned examples prove that the applied biocompatible hydrophilic gel can be made using the applied method.

The applied hydrophilic gel virtually does not cause any tissue response, sensitization or any dystrophic/necrotic changes in a recipient's body and is suitable for implantation into a human or animal body where it becomes a basis for formation of a capsule and serves as a carrier for subsequently implanted selected cell cultures.

As compared to a known prototype gel (Formacryl hydrophilic gel), the applied gel does not contain free $NH_2$-radicals that could fit into the structural network of the hydrophilic gel by means of coordinate bonding.

As compared to the prototype, the applied hydrophilic gel has more close-meshed structure and can be used as a carrier for culturing the implanted cells in a recipient's body for a longer time, maintaining them viable and capable of producing substances essential for the recipient, such as testosterone and insulin.

The invention claimed is:

1. Multifunctional biocompatible hydrophilic gel containing polyacrylamide and water, distinguished by that it contains as the polyacrylamide a cross-linked copolymer of acrylamide, methacrylamide and cross-linking agents which are 2-hydroxyethyl methacrylate and N,N'-methylene-bis-acrylamide, wherein it contains components in the following proportions (w/w %):

acrylamide—1.95-8.0,
methacrylamide—0.54-3.0,
2-hydroxyethyl methacrylate—0.003-0.4,
N,N'-methylene-bis-acrylamide—0.006-0.6,
water—sufficient quantity to 100.

2. Multifunctional biocompatible hydrophilic gel per claim 1, wherein the above mentioned polyacrylamide makes up from 3.0 to 10.0% (w/w) of the total weight of the biocompatible hydrophilic gel.

3. Multifunctional biocompatible hydrophilic gel per claim 1, wherein it contains bidistilled apyrogenic water as water.

4. Multifunctional biocompatible hydrophilic gel per claims 3, wherein it has pH 3.5-4.5.

5. Multifunctional biocompatible hydrophilic gel per claim 1, wherein it is suitable for injection.

6. Multifunctional biocompatible hydrophilic gel per claim 1, wherein it is suitable for formation of a capsule in human and animal tissues.

7. Multifunctional biocompatible hydrophilic gel per claim 1, wherein it is suitable for using as carrier for culturing heterogeneous (allogenic or xenogenic) or autoimmune cells.

8. Multifunctional biocompatible hydrophilic gel per claim 5, wherein it is packed in syringes.

* * * * *

UNITED STATES PATENT AND TRADEMARK OFFICE
CERTIFICATE OF CORRECTION

| | |
|---|---|
| PATENT NO. | : 7,238,761 B2 |
| APPLICATION NO. | : 10/937472 |
| DATED | : July 3, 2007 |
| INVENTOR(S) | : Vladislav Victorovich Lopatin |

Page 1 of 1

It is certified that error appears in the above-identified patent and that said Letters Patent is hereby corrected as shown below:

Title page, item 73, "Organichennoy" should read -- Ogranichennoy --.

Signed and Sealed this

Eighteenth Day of September, 2007

JON W. DUDAS
*Director of the United States Patent and Trademark Office*